(12) United States Patent
Byrd

(10) Patent No.: US 12,414,814 B2
(45) Date of Patent: Sep. 16, 2025

(54) PULMONARY VEIN ISOLATION BALLOON CATHETER

(71) Applicant: ST. JUDE MEDICAL, CARDIOLOGY DIVISION, INC., St. Paul, MN (US)

(72) Inventor: Israel A. Byrd, Richfield, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 542 days.

(21) Appl. No.: 16/468,525

(22) PCT Filed: Dec. 4, 2017

(86) PCT No.: PCT/US2017/064532
§ 371 (c)(1),
(2) Date: Jun. 11, 2019

(87) PCT Pub. No.: WO2018/111600
PCT Pub. Date: Jun. 21, 2018

(65) Prior Publication Data
US 2020/0008869 A1    Jan. 9, 2020

Related U.S. Application Data

(60) Provisional application No. 62/434,828, filed on Dec. 15, 2016.

(51) Int. Cl.
*A61B 18/14*       (2006.01)
*A61B 18/02*       (2006.01)
(Continued)

(52) U.S. Cl.
CPC .......... *A61B 18/1492* (2013.01); *A61B 18/02* (2013.01); *A61B 18/1206* (2013.01);
(Continued)

(58) Field of Classification Search
CPC .. A61B 2018/1266; A61B 2018/00613; A61B 2018/0022
See application file for complete search history.

(56) References Cited

U.S. PATENT DOCUMENTS 6,254,599 B1    7/2001   Lesh et al.
6,291,568 B1    9/2001   Lussey
(Continued)

FOREIGN PATENT DOCUMENTS

CN    102961183 A    3/2013
CN    104644161 A    5/2015
(Continued)

OTHER PUBLICATIONS

International Search Report for Chinese Patent Application No. 2021112984904, Jan. 18, 2024, 2 pages.

*Primary Examiner* — Linda C Dvorak
*Assistant Examiner* — Christine A Dedoulis
(74) *Attorney, Agent, or Firm* — Armstrong Teasdale LLP

(57) ABSTRACT

The instant disclosure relates to electrophysiology catheters for tissue ablation within a cardiac muscle. In particular, the instant disclosure relates to an electrophysiology ablation balloon catheter with conductive and non-conductive surfaces for focusing ablation energy at a desired portion of pulmonary vein tissue.

16 Claims, 6 Drawing Sheets

(51) Int. Cl.
  *A61B 18/12* (2006.01)
  *A61B 18/00* (2006.01)
(52) U.S. Cl.
  CPC ........... *A61B 2018/00029* (2013.01); *A61B 2018/00077* (2013.01); *A61B 2018/00083* (2013.01); *A61B 2018/00101* (2013.01); *A61B 2018/0022* (2013.01); *A61B 2018/00404* (2013.01); *A61B 2018/00577* (2013.01); *A61B 2018/00613* (2013.01); *A61B 2018/00839* (2013.01); *A61B 2018/0212* (2013.01); *A61B 2018/1266* (2013.01)

(56) References Cited

U.S. PATENT DOCUMENTS

| | | | |
|---|---|---|---|
| 6,416,511 B1 * | 7/2002 | Lesh | A61B 18/00 606/41 |
| 6,495,069 B1 | 12/2002 | Lussey et al. | |
| 6,646,540 B1 | 11/2003 | Lussey | |
| 6,952,615 B2 | 10/2005 | Satake | |
| 6,999,821 B2 | 2/2006 | Jenney et al. | |
| 7,112,198 B2 | 9/2006 | Satake | |
| 7,736,362 B2 | 6/2010 | Eberl et al. | |
| 7,955,326 B2 | 6/2011 | Paul et al. | |
| 8,231,617 B2 | 7/2012 | Satake | |
| 8,500,730 B2 | 8/2013 | Lee et al. | |
| 8,647,339 B2 | 2/2014 | Satake | |
| 9,237,925 B2 * | 1/2016 | Fischell | A61B 18/1492 |
| 2001/0041890 A1 | 11/2001 | Hassett et al. | |
| 2004/0116965 A1 | 6/2004 | Falkenberg | |
| 2004/0260277 A1 | 12/2004 | Maguire | |
| 2005/0059965 A1 | 3/2005 | Eberl et al. | |
| 2005/0070887 A1 | 3/2005 | Taimisto et al. | |
| 2005/0203597 A1 | 9/2005 | Yamazaki et al. | |
| 2007/0083192 A1 * | 4/2007 | Welch | A61B 18/1492 606/41 |
| 2009/0157066 A1 | 6/2009 | Satake | |
| 2010/0179530 A1 | 7/2010 | Long et al. | |
| 2010/0204560 A1 * | 8/2010 | Salahieh | A61B 5/01 606/41 |
| 2011/0301587 A1 * | 12/2011 | Deem | A61B 18/1815 606/41 |
| 2012/0010612 A1 | 1/2012 | Lesh | |
| 2013/0030425 A1 * | 1/2013 | Stewart | A61B 18/02 606/24 |
| 2013/0197497 A1 | 8/2013 | Wittenerger et al. | |
| 2013/0204068 A1 * | 8/2013 | Gnanashanmugam | A61B 18/18 601/3 |
| 2014/0378966 A1 | 12/2014 | Haverkost et al. | |
| 2015/0141982 A1 | 5/2015 | Lee | |
| 2017/0035499 A1 * | 2/2017 | Stewart | A61N 1/327 |
| 2017/0354463 A1 | 12/2017 | Mori | |

FOREIGN PATENT DOCUMENTS

| | | |
|---|---|---|
| CN | 105708544 A | 6/2016 |
| JP | 2015112114 | 6/2015 |
| JP | 2016185295 A | 10/2016 |
| WO | 199732532 | 9/1997 |
| WO | 2010080974 | 7/2010 |
| WO | 2017074920 A1 | 5/2017 |

* cited by examiner

PULMONARY VEIN ISOLATION BALLOON CATHETER

CROSS-REFERENCE TO RELATED APPLICATION

This application claims the benefit of U.S. Provisional Application No. 62/434,828, filed 15 Dec. 2016.

BACKGROUND a. Field

The instant disclosure relates to catheters; in particular, catheters for conducting ablation therapy within a heart. In one embodiment, the instant disclosure relates to a catheter for treating cardiac arrhythmias by ablating in the vicinity of pulmonary venous tissue.

b. Background Art

The human heart routinely experiences electrical currents traversing its myocardial tissue. After each heart contraction the heart repolarizes, causing electrical currents to spread through the myocardial tissue. In healthy hearts, the tissue of the heart will experience an orderly progression of depolarization waves. In unhealthy hearts, such as those experiencing atrial arrhythmia, including for example, ectopic atrial tachycardia, atrial fibrillation, and atrial flutter, the progression of the depolarization wave becomes chaotic. Arrhythmias may persist as a result of scar tissue or other obstacles to rapid and uniform depolarization. These obstacles may cause depolarization waves to electrically circulate through some parts of the heart more than once. Atrial arrhythmia can create a variety of dangerous conditions, including irregular heart rates, loss of orderly atrial and ventricular contractions, and blood flow stasis. All of these conditions have been associated with a variety of ailments, including death.

Catheters are used in a variety of diagnostic and/or therapeutic medical procedures to correct conditions such as atrial arrhythmia, including for example, ectopic atrial tachycardia, atrial fibrillation, and atrial flutter.

Typically in an intravascular procedure, a catheter is manipulated through a patient's vasculature to, for example, a patient's heart, and carries one or more electrodes which may be used for mapping, ablation, diagnosis, or other treatments. Where an ablation therapy is desired to alleviate symptoms including atrial arrhythmia, an ablation catheter imparts ablative energy to myocardial tissue to create a lesion. The lesioned tissue is less capable of conducting electrical signals, thereby disrupting undesirable electrical pathways and limiting or preventing stray electrical signals that lead to arrhythmias. The ablation catheter may utilize ablative energy including, for example, radio frequency (RF), cryoablation, laser, chemical, and high-intensity focused ultrasound. As readily apparent, such an ablation treatment requires precise positioning of the ablation catheter for optimal results.

The foregoing discussion is intended only to illustrate the present field and should not be taken as a disavowal of claim scope.

BRIEF SUMMARY

The instant disclosure relates to electrophysiology catheters for tissue ablation within the heart. In particular, the instant disclosure relates to an electrophysiology ablation balloon catheter with conductive and non-conductive surfaces for focusing ablative energy at a desired portion of tissue.

In one exemplary embodiment of the present disclosure, an ablation balloon apparatus is disclosed. The ablation balloon apparatus includes a catheter shaft, and an ablation balloon, where a proximal end of the ablation balloon is coupled to a distal end of the catheter shaft. The ablation balloon includes a conductive portion and a non-conductive portion. The conductive portion may facilitate energy transfer between the ablation balloon and tissue in contact with the conductive portion, while the non-conductive portion mitigates energy transfer between the ablation balloon and tissue in contact with the non-conductive portion.

In another embodiment of the present disclosure, a system for treating atrial fibrillation is disclosed. The system includes an elongated shaft, a balloon delivery catheter and an ablation balloon. The elongated shaft includes a lumen extending through the elongated shaft, which the balloon delivery catheter extends through. The ablation balloon includes a conductive portion and a non-conductive portion, and is coupled to a distal end of the balloon delivery catheter. The ablation balloon may engage with a tissue wall of a pulmonary vein along the conductive portion of the ablation balloon, and deliver an ablation therapy along the tissue wall of the pulmonary vein engaged by the conductive portion of the balloon.

Other embodiments of the present disclosure are directed to a balloon catheter for pulmonary vein isolation. In such an embodiment, the balloon catheter includes a steerable balloon delivery catheter shaft, an ablation balloon, and a tissue ablation means. The steerable balloon delivery catheter shaft deploys the ablation balloon into a pulmonary vein, and the ablation balloon includes a conductive region at a distal end of the balloon delivery catheter. The ablation balloon, in response to being deployed, may engage a tissue wall of the pulmonary vein along the conductive portion of the ablation balloon. The tissue ablation means, in conjunction with the ablation balloon, delivers an ablation therapy to the tissue wall of the pulmonary vein along the conductive portion of the ablation balloon.

The foregoing and other aspects, features, details, utilities, and advantages of the present disclosure will be apparent from reading the following description and claims, and from reviewing the accompanying drawings.

BRIEF DESCRIPTION OF THE DRAWINGS

Various example embodiments may be more completely understood in consideration of the following detailed description in connection with the accompanying drawings.

Figure 1:
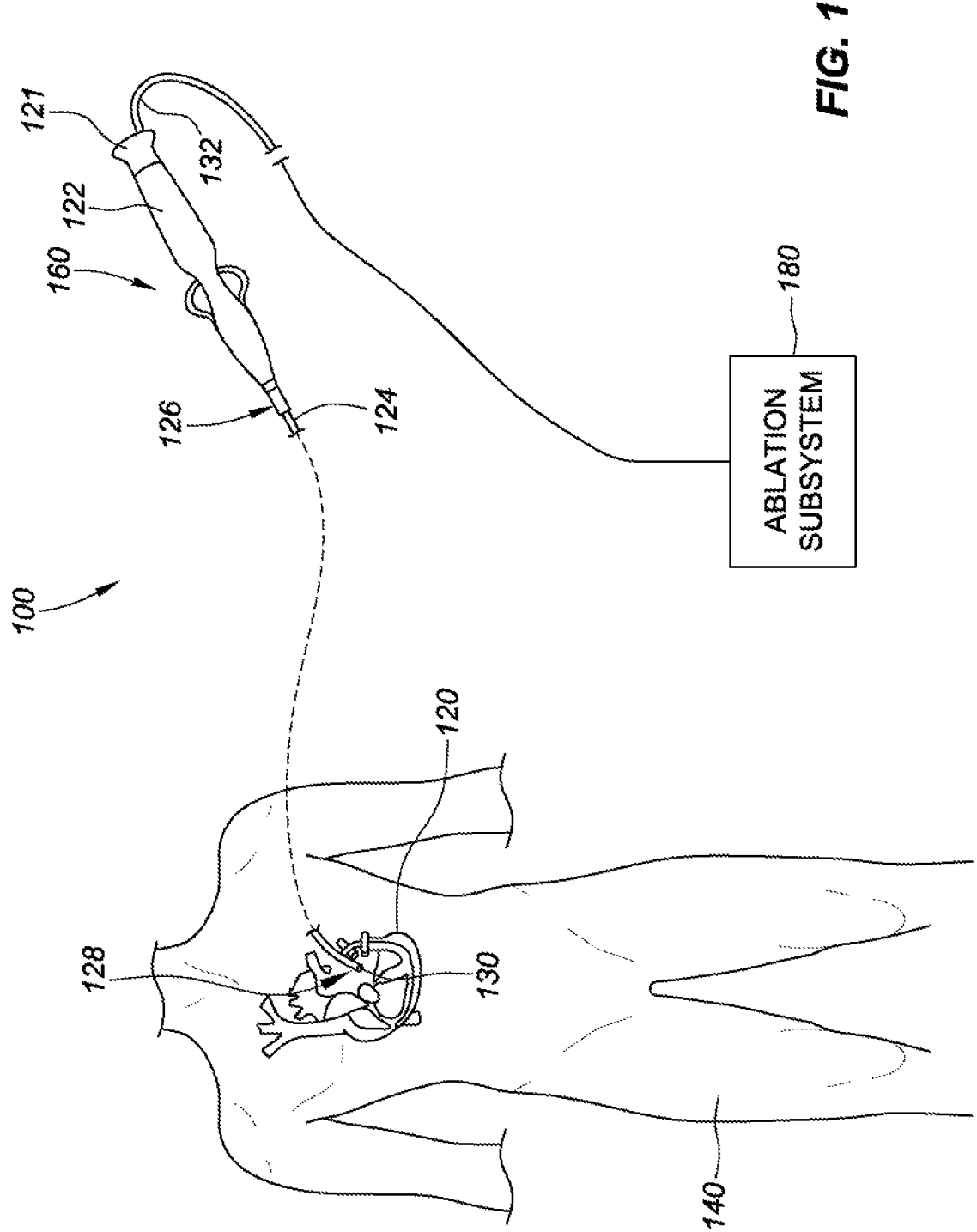
FIG. 1 is a schematic and diagrammatic view of a catheter system for performing a therapeutic medical procedure, consistent with various aspects of the present disclosure.

While various embodiments discussed herein are amenable to modifications and alternative forms, aspects thereof have been shown by way of example in the drawings and will be described in detail. It should be understood, however, that the intention is not to limit the scope to the particular embodiments described. On the contrary, the intention is to cover all modifications, equivalents, and alternatives falling within the scope of the disclosure including aspects defined in the claims. In addition, the term "example" as used throughout this application is only by way of illustration, and not limitation.

DETAILED DESCRIPTION OF EMBODIMENTS

The instant disclosure relates to electrophysiology catheters for tissue ablation within the heart, for example. In particular, the instant disclosure relates to an electrophysiology ablation balloon catheter with conductive and non-conductive surfaces for focusing ablative energy at a desired portion of tissue (e.g., pulmonary venous tissue). Details of the various embodiments of the present disclosure are described below with specific reference to the figures.

Typically, ablation therapies have been delivered by making a number of individual ablations in a controlled fashion in order to form a lesion line. Such lesion lines are often desirably formed around/between the pulmonary veins in the left atrium of the heart which have been associated with the introduction point of erratic electric signals into the heart. There are devices in development, or being commercialized, that attempt to achieve a sufficient block of ablations with minimal applications of energy. Existing designs range from diagnostic catheters with hoop and balloon mounted designs including energy applying features. Existing designs suffer from a lack of ability to focus ablation energy at a target circumference and length of the pulmonary vein during therapy delivery, resulting in energy loss to the blood pool and unintentional ablation of non-target tissue. Moreover, the resulting energy loss may reduce the efficacy of target tissue ablation, and cause inconsistent lesion lines and incomplete electrical signal blockage.

Referring now to the drawings wherein like reference numerals are used to identify similar components in the various views, FIG. 1 is a schematic and diagrammatic view of a catheter ablation system 100 for performing a tissue ablation procedure. In one example embodiment, tissue 120 comprises cardiac tissue within a human body 140. It should be understood, however, that the system may find application in connection with a variety of other tissue within human and non-human bodies, and therefore, the present disclosure is not meant to be limited to the use of the system in connection with only cardiac tissue and/or human bodies.

Catheter ablation system 100 may include a catheter 160 and an ablation subsystem 180 for controlling an ablation therapy conducted by an ablation balloon 130 at a distal end 128 of the catheter 160. The ablation subsystem 180 can control the application of and/or generation of ablative energy including, for example, radio frequency (RF), cryoablation, laser, chemical, and high-intensity focused ultrasound.

In the exemplary embodiment of FIG. 1, catheter 160 is provided for examination, diagnosis, and/or treatment of internal body tissue such as cardiac tissue 120. The catheter may include a cable connector or interface 121, a handle 122, a shaft 124 having a proximal end 126 and a distal end 128 (as used herein, "proximal" refers to a direction toward the end of the catheter 160 near the handle 122, and "distal" refers to a direction away from the handle 122), and an ablation balloon 130 coupled to the distal end 128 of the catheter shaft 124.

Ablation balloon 130 may be manipulated through vasculature of a patient 140 using handle 122 to steer one or more portions of shaft 124, and position the ablation balloon at a desired location (e.g., within a heart muscle). In various embodiments, the ablation balloon includes ablation elements (e.g., ablation electrodes, high intensity focused ultrasound ablation elements, super cooled/heated fluid, etc.) that when operated by ablation subsystem 180 ablates the tissue 120 in contact with the ablation balloon 130 (and in some cases tissue in proximity to the ablation balloon 130 may be ablated by conductive energy transfer through the blood pool to the proximal tissue).

In various specific embodiments of the present disclosure, catheter 160 may include electrodes and one or more positioning sensors at a distal end 128 of catheter shaft 124 (e.g., electrodes and/or magnetic sensors). In such an embodiment, the electrodes acquire EP data relating to cardiac tissue 120, while the positioning sensor(s) generate positioning data indicative of the 3-D position of the ablation balloon 130. In further embodiments, the catheter 160 may further include other conventional catheter components such as, for example and without limitation, steering wires and actuators, irrigation lumens and ports, pressure sensors, contact sensors, temperature sensors, additional electrodes, and corresponding conductors or leads.

Connector 121 provides mechanical and electrical connection(s) for one or more cables 132 extending, for example, from ablation subsystem 180 to ablation balloon 130. In other embodiments, the connector may also provide mechanical, electrical, and/or fluid connections for cables extending from other components in catheter system 100, such as, for example, a fluid source (when the catheter 160 comprises an irrigated catheter) and contact/pressure sensing circuitry. The connector 121 is conventional in the art and is disposed at a proximal end 126 of the catheter 160.

Handle 122 provides a location for a user to hold catheter 160 and may further provide steering or guidance for the shaft 124 within the body 140. For example, the handle 122 may include means to manipulate one or more steering wires extending through the catheter 160 to a distal end 128 of the shaft 124, thereby steering the shaft. The handle 122 is conventional in the art and it will be understood that the construction of the handle may vary. In other embodiments, control of the catheter 160 may be automated by robotically driving or controlling the catheter shaft 124, or driving and controlling the catheter shaft 124 using a magnetic-based guidance system.

Catheter shaft 124 is an elongated, tubular, and flexible member configured for movement within a patient's body 140. The shaft supports an ablation balloon 130 at a distal end 128 of catheter 160. The shaft 124 may also permit transport, delivery and/or removal of fluids (including irrigation fluids, cryogenic ablation fluids, and body fluids), medicines, and/or surgical tools or instruments. The shaft 124, which may be made from conventional materials used for catheters, such as polyurethane, defines one or more lumens configured to house and/or transport electrical conductors, fluids, and/or surgical tools. The catheter may be introduced into a blood vessel or other structure within the body 140 through a conventional introducer sheath.

In an exemplary cardiac ablation therapy, to correct for atrial arrhythmia, the introducer sheath is introduced through a peripheral vein (typically a femoral vein) and advanced into the right atrium, in what is referred to as a transeptal approach. The introducer sheath then makes an incision in the fossa ovalis (the tissue wall between the left and right atriums), and extends through the incision in the fossa ovalis to anchor the introducer sheath therein. The ablation catheter 160 may then be extended through a lumen of the introducer sheath into the left atrium. Catheter shaft 124 of ablation catheter 160 may then be steered or guided through the left atrium to position an ablation balloon 130 into a desired location within the left atrium such as a pulmonary vein.

To achieve effective and efficient ablation of target myocardial tissue in contact with an ablation balloon 130, energy transfer through the ablation balloon must be focused in a way that limits energy transfer through portions of the balloon that are not in contact with the target myocardial tissue. For example, in a cryoablation balloon application, cryofluid (also known as cryogenic fluid) being injected into the balloon cools not only the portion of the balloon in contact with the target tissue, but also other portions of the balloon that act as a heat sink with the blood pool and non-target tissue; such unintentional energy loss impedes the effectiveness of the tissue ablation therapy as precise energy applied to the target tissue is unknown and efficiency of the cryofluid is greatly impeded due to the various non-target heat sinks. Accordingly, aspects of the present disclosure focus energy transfer through the ablation balloon by implementing conductive and non-conductive regions on a surface of the balloon (or within the balloon itself). The non-conductive portions may be placed in areas where target tissue is unlikely to contact the surface of the ablation balloon and insulates these portions to prevent undesirable energy transfer. The conductive portions may be placed in areas where target tissue is likely to contact the surface of the ablation balloon and transfer energy between the ablation balloon and tissue in contact with the conductive portion—thereby focusing energy use to the target tissue areas and reducing overall cryofluid required for a given therapy.

In applications utilizing direct current electroporation pulses and/or radio frequencies to conduct tissue ablation therapy, the conductive regions may help facilitate the flow of radio waves and/or electrical pulses. In such applications, the non-conductive regions may act to shield non-target tissue from the radio waves and/or electrical pulses emanating from the ablation balloon. In some specific embodiments, electrical shielding within the non-conductive portions of the ablation balloon may reflect back the radio waves and/or electrical pulses emitted from within the ablation balloon and increase the intensity/strength of the resulting radio waves and/or electrical pulses emitted from the conductive portion(s) of the ablation balloon.

Figure 2:
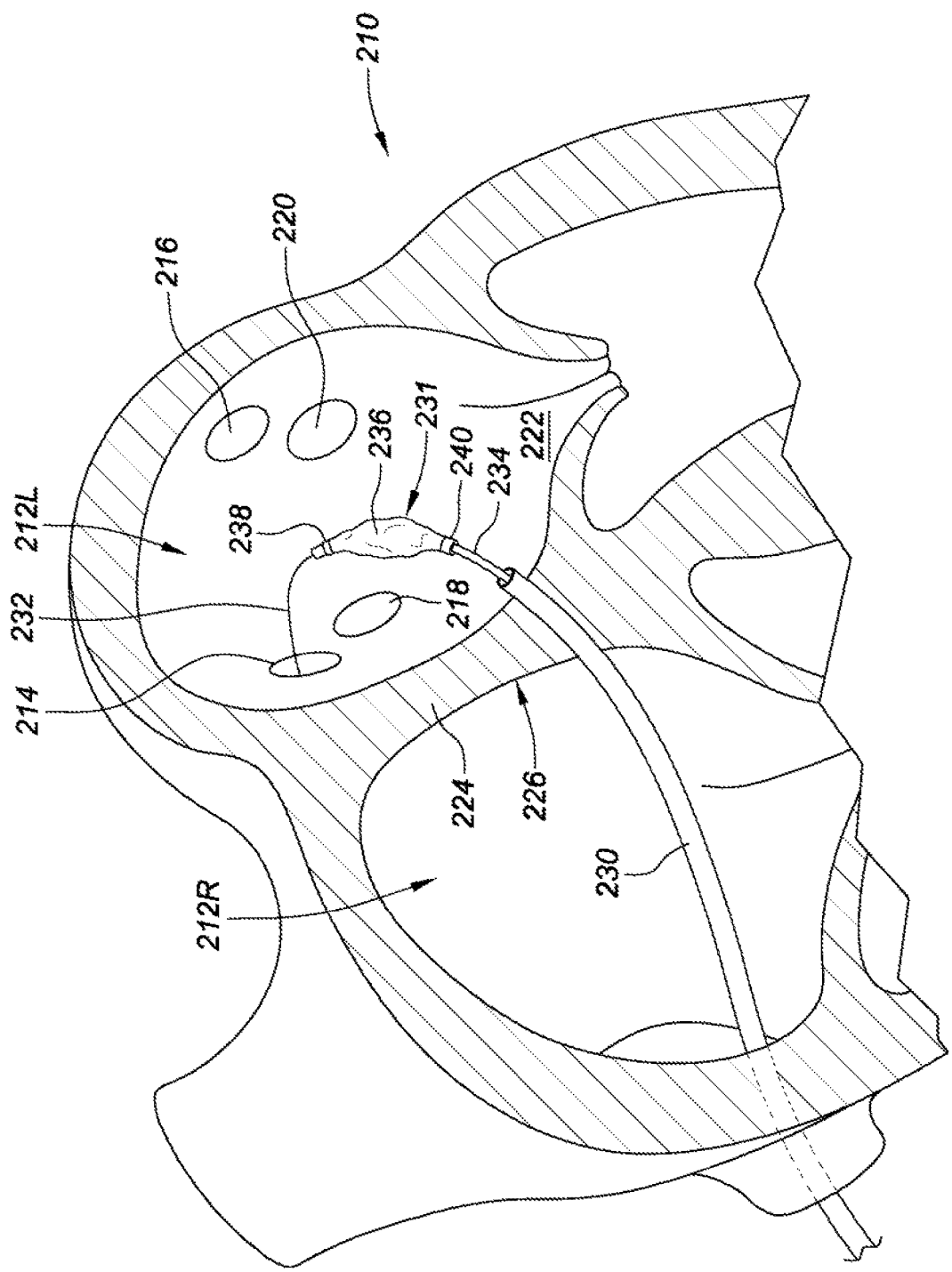
FIG. 2 is a cross-sectional front-view of a left atrium with an ablation balloon catheter locating a pulmonary vein, consistent with various aspects of the present disclosure.

FIG. 2 is a cross-sectional front-view of a portion of cardiac muscle 210 with an ablation balloon catheter 231 locating a pulmonary vein (e.g., 214, 216, 218, and 220) for performing ablation therapy therein. Ablation therapy can minimize symptoms related to, for example, atrial fibrillation. As shown in FIG. 2, the cardiac muscle 210 includes two upper chambers called the left atrium 212L and right atrium 212R, and two lower chambers called the left ventricle and right ventricle (partially visible).

Aspects of the present disclosure are directed to ablation therapies in which tissue in (or adjacent to) pulmonary veins 214, 216, 218, and 220, which form conductive pathways for electrical signals traveling through the tissue, is destroyed in order to electrically isolate sources of unwanted electrical impulses (e.g., arrhythmiatic foci) located in the pulmonary veins. By either destroying the arrhythmiatic foci, or electrically isolating them from the left atrium 212L, the cause of atrial symptoms can be reduced or eliminated.

As shown in FIG. 2, an ablation balloon catheter 231 may be introduced into the left atrium 212L by an introducer sheath 230. A guidewire 232 and catheter shaft 234 may guide the ablation balloon 236, once introduced into the left atrium 212L by the introducer sheath 230. Optionally, the ablation balloon catheter 231 may include mapping electrodes at proximal and distal ends of ablation balloon, 240 and 238, respectively. In operation, introducer sheath 230 has its distal end positioned within left atrium 212L. As shown in FIG. 2, a transeptal approach may be utilized in which introducer sheath 230 is introduced through a peripheral vein (typically a femoral vein) and advanced to right atrium 212R. The introducer sheath 230 makes a small incision into the fossa ovalis 224 which allows the distal end of the introducer sheath 230 to enter the left atrium 212L (through the transeptal wall 226) and to anchor itself to the wall of the fossa ovalis 224.

Ablation balloon catheter 231 may also be introduced into left atrium 212L through the arterial system. In that case, introducer sheath 230 is introduced into an artery (such as a femoral artery) and advanced retrograde through the artery to the aorta, the aortic arch, and into the left ventricle. The ablation balloon catheter 231 is then extended from within a lumen of the introducer sheath 230 to enter the left atrium 212L through mitral valve 222.

Once introducer sheath 230 is in position within left atrium 212L, steerable ablation balloon catheter 231 is advanced out a distal end of the introducer sheath 230 and toward one of the pulmonary veins (e.g., 214, 216, 218, and 220). In FIG. 2, the target pulmonary vein is right superior pulmonary vein 214. A guidewire 232 and a catheter shaft 234 of the ablation balloon catheter 231 are manipulated until the distal tip of the ablation balloon catheter is directed toward the target pulmonary vein, after which the ablation balloon is extended into the pulmonary vein 214.

Carried near a distal end of ablation balloon catheter 231, ablation balloon 236 remains in a collapsed condition so that it may pass through introducer sheath 230, and enter target pulmonary vein 214. Once in position, the ablation balloon 236 is deployed, so that it engages and secures the ablation balloon catheter 231 within the target pulmonary vein 214.

As optionally shown, the embodiment of FIG. 2 may include mapping electrodes 238 and 240. The mapping electrodes 238 and 240 may be ring electrodes that allow a clinician to perform a pre-deployment electrical mapping of the conduction potentials of the pulmonary vein 214.

Although shown as being carried on ablation balloon catheter 231, mapping electrodes may alternatively be carried on-board a separate electrophysiology catheter (e.g., on-board a loop catheter). In various other embodiments, the electrodes may also be positioned on an outer surface of the ablation balloon 236. After an ablation therapy is complete, the clinician may again utilize the mapping electrodes 238 and 240 to map the conduction potentials of the pulmonary vein to determine the efficacy of the ablation therapy.

To ablate tissue, once deployed, ablation balloon 236 may electrically conduct a DC energy current into the targeted tissue of the pulmonary vein 214 (also referred to as electroporation). In other embodiments, the ablation balloon 236 may transmit radio-frequency energy to ablate the target tissue. In yet other embodiments, the ablation balloon 236 may deliver one or more of the following energies to the targeted tissue: cryoablation, laser, chemical, and high-intensity focused ultrasound, among others.

In various embodiments consistent with the above implementations, ablation balloon 236 may also include non-conductive sections of the ablation balloon 236 that insulate, shield, resist, limit, or otherwise mitigate the flow of the ablation energy there through. In specific implementations, the non-conductive sections are aligned with tissue that is not targeted for ablation therapy; whereas conductive regions of the ablation balloon 236 are positioned to contact targeted tissue portions for the ablation therapy. Accordingly, various ablation balloon implementations are envisioned including an ablation balloon for ablating a pulmonary vein antrum. In such an embodiment, a distal portion of the ablation balloon may consist of a conductive portion for allowing the transfer of ablative energy between the conductive portion of the ablation balloon and the pulmonary vein antrum. In such an embodiment, the proximal portion of the ablation balloon may also consist of a non-conductive portion to prevent ablative energy from being directed away from the antrum of the pulmonary vein by a blood pool heat sink and/or non-target tissue, for example. Yet other ablation balloon implementations consistent with the present disclosure are directed to ablating a pulmonary vein ostium. In such an embodiment, a central circumferential portion of the ablation balloon consists of a conductive portion for affecting ablation therapy to a target portion of the pulmonary vein ostium. In such an embodiment, the proximal and distal portions of the ablation balloon may also comprise non-conductive portions to prevent the ablative energy from being directed away from the pulmonary vein ostium by a blood pool heat sink and/or non-target tissue (e.g., pulmonary vein antrum).

Figure 3:
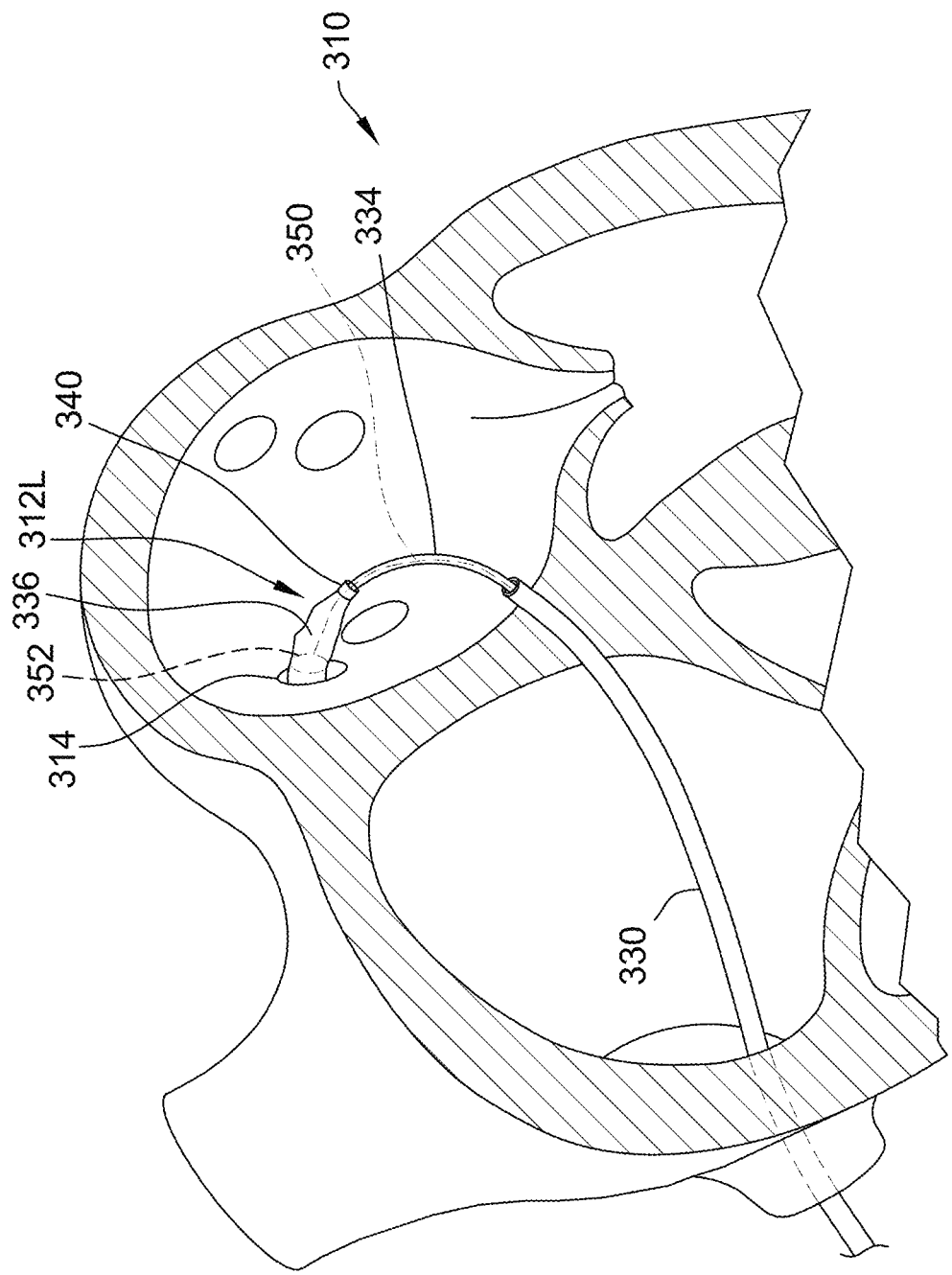
FIG. 3 is a cross-sectional front-view of a left atrium with the ablation balloon catheter of FIG. 2 positioned within a pulmonary vein, consistent with various aspects of the present disclosure.

FIG. 3 shows an ablation balloon catheter 331 including an ablation balloon 336 advancing into an antrum of pulmonary vein 314 (by extending out of introducer sheath 330). As the ablation balloon catheter 331 enters the pulmonary vein 314, mapping may be conducted using electrodes, 338 (hidden from view) and 340, in order to verify proper location prior to deployment of the ablation balloon 336.

It has been discovered that augmenting ablation balloons 336 with conductive and non-conductive portions may more effectively transfer energy into/out of the ablation balloon 336. In various embodiments of the present disclosure, the conductive and non-conductive portions may be integral to the expandable ablation balloon (e.g., a material additive such as metal dust), coupled to an interior and/or exterior surface of the ablation balloon, comprise an additional/ separate layer within the ablation balloon 336, or comprise one layer of a dual layer balloon set-up with a conductive/ non-conductive balloon positioned within an outer ablation balloon (or vice versa). In yet further more specific embodiments, each of the conductive and non-conductive portions may comprise its own segment of a balloon that is free-standing relative to the other layer and the expandable ablation balloon itself. In such embodiments, the conductive and non-conductive portions may be adjustable via a pull wire or other adjustment mechanism to vary the location of the conductive and non-conductive portions. By dynamically adjusting the position of the conductive and non-conductive portions, the focus of the energy transfer system of the ablation balloon 336 may be adjusted to various portions of a pulmonary vein in contact with the balloon.

In one specific application, where a therapy is being conducted to treat a patient suffering from atrial fibrillation symptoms—an ablation balloon 336 (consistent with the present disclosure) engages inner walls of a target pulmonary vein 314. Once in position, conductive and non-conductive baffles 352 within the ablation balloon may be positioned to focus energy transfer using pull wires 350 and/or steering wires extending the length of catheter shaft 334. For the first therapy, the conductive and non-conductive baffles 352 may be positioned to minimize transfer of energy through distal and proximal portions of the ablation balloon by positioning the non conductive portions in proximity thereto; accordingly, the conductive baffle 352 may be positioned near a central portion of the ablation balloon. Such a configuration may be implemented for ablating a pulmonary vein ostium. In some embodiments no conductive baffle may be necessary where the ablation balloon material is conductive. Using one or more of the energy transfer systems discussed above, the ablation balloon focuses a transfer of energy at tissue of the pulmonary vein ostium, while minimizing energy transfer to other areas of the pulmonary vein tissue by shielding, insulating, reflecting, or otherwise mitigating the flow of energy through the non-conductive baffles 352. The therapy creates a circumferential zone of ablation around an inner wall of the pulmonary vein ostium. The ablation zone electrically isolates the target pulmonary vein 314 from left atrium 312L. To the extent that arrhythmiatic foci were located within the ablation zone, the arrhythmiatic foci are destroyed. To the extent the arrhythmiatic foci are located in the target pulmonary vein on the opposite side of the ablation zone from the left atrium, the electrical impulses produced by those foci are blocked or substantially inhibited by the ablation zone.

After the ablation therapy at a pulmonary vein ostium is complete, the ablation balloon may be collapsed for removal from the cardiac muscle 310, or may be repositioned and/or reconfigured to conduct additional ablation therapies to other pulmonary veins (e.g., 316, 318, and 320) and/or to other portions of the target pulmonary vein 314 (e.g., pulmonary vein antrum). For example, the conductive and non-conductive baffles 352 may be reconfigured and the ablation balloon 336 repositioned to conduct ablation therapy to an antrum of the target pulmonary vein 314. In such an application, a distal portion of the ablation balloon is positioned into contact with the antral portion of the target pulmonary vein, and the non-conductive baffles 352 are repositioned, via the guide wires, to the proximal portion of the ablation balloon. Using one or more of the energy transfer systems discussed above, the ablation balloon focuses a transfer of energy at tissue of the antral portion of the pulmonary vein, while minimizing energy transfer into the blood pool and to other areas of the pulmonary vein tissue by shielding, insulating, reflecting, or otherwise mitigating the flow of energy through the non-conductive baffles 352. The therapy creates a circumferential zone of ablation around the antral portion of the pulmonary vein that electrically isolates the target pulmonary vein 314 from left atrium 312L.

Figure 4:
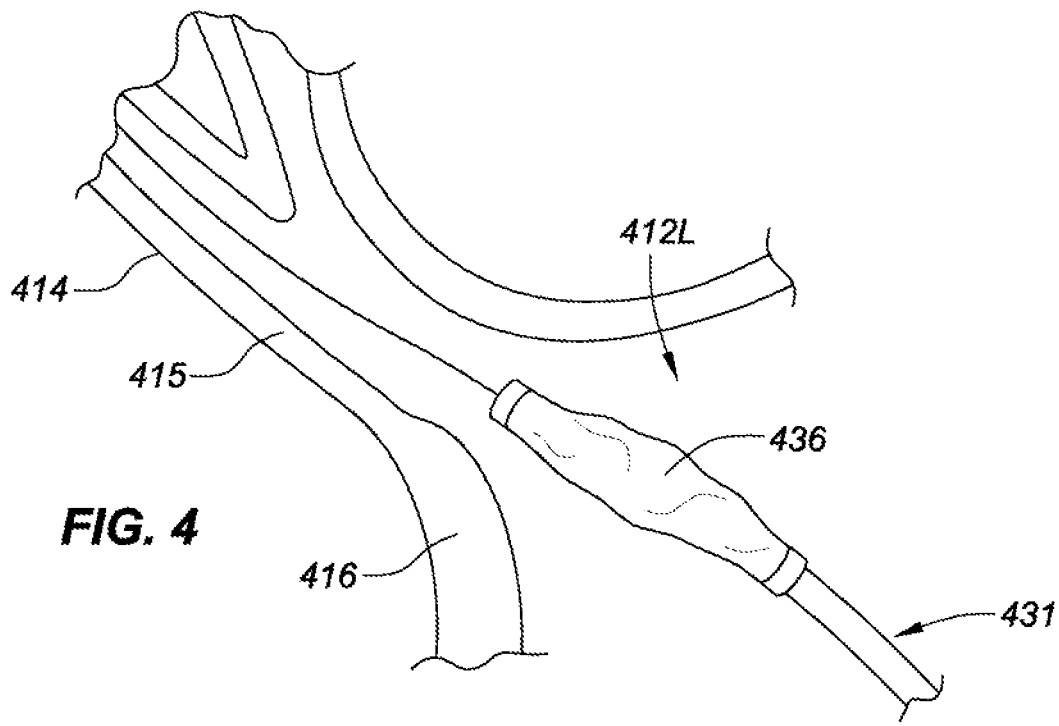
FIG. 4 is a cross-sectional front-view of a pulmonary vein with the ablation balloon catheter of FIG. 2 positioned therein, prior to deployment of the ablation balloon, consistent with various aspects of the present disclosure.

FIG. 4 shows ablation balloon catheter 431 with ablation balloon 436 in position near target pulmonary vein 414 prior to balloon deployment. As shown in FIG. 4, the ablation balloon catheter 431 is being steered into position near an antrum 416 of the target pulmonary vein 414. Before arriving within the antrum 416, the ablation balloon catheter 431 must steer the ablation balloon 436 through the left atrium 412L and into proximity with the target pulmonary vein 414. In the present embodiment, the ablation balloon catheter 431 is being positioned to conduct an ablation therapy at the antrum 416 of the target pulmonary vein 414. In such a procedure, once the ablation balloon is expanded into contact with the antrum 416, an ablation therapy may be initiated that ablates a circumferential zone of ablation around the antrum 416. The circumferential zone of ablation electrically isolates the left atrium 412L from electrical impulses produced by arrhythmiatic foci opposite the ablation. In some embodiments of the present disclosure, precisely locating the ablation balloon catheter 431 may greatly affect the efficacy of the ablation therapy; accordingly, some embodiments of the present disclosure properly locate the ablation balloon within the target pulmonary vein 414 by mapping, prior to deployment of the ablation balloon, using electrodes proximal and distal the ablation balloon 436 (as shown in FIGS. 2 and 3).

Figure 5:
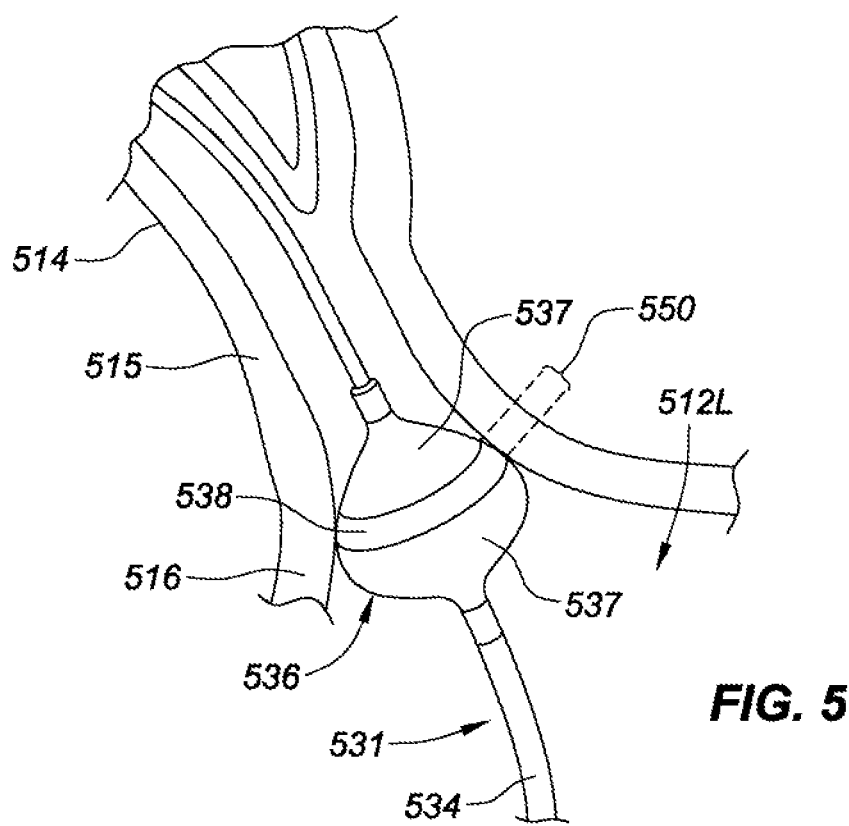
FIG. 5 is a cross-sectional front-view of a pulmonary vein with the ablation balloon catheter of FIG. 2 deployed therein, consistent with various aspects of the present disclosure.

FIG. 5 shows an ablation balloon catheter 531 with an expanded ablation balloon 536 engaged within an antrum 516 of target pulmonary vein 514. Shaft 534 of the ablation balloon catheter 531 extends out of the antrum 516 of the target pulmonary vein 514 and into left atrium 512L. The expanded shape of the ablation balloon 536 is designed to contour to at least a length and circumference of the antrum 516 of the pulmonary vein 514. Aspects of the present disclosure are directed to the ablation balloon 536 including conductive and nonconductive portions, 538 and 537, respectively. In one embodiment, the ablation balloon is a cryoablation balloon that may be filled with cryogenic fluid to fill and cool the ablation balloon to ablate tissue in contact therewith (and in some circumstances, tissue in proximity to the ablation balloon). The conductive portion 538 may be located around a central circumference of the ablation balloon 536, and facilitate ablation of tissue in contact with the conductive portion 538 by thermally transferring energy from the antrum 516 of the pulmonary vein 514, in contact with the conductive portion 538, to the ablation balloon 536. The ablation balloon may also include non-conductive portions 537 on the proximal and distal ends of the balloon that insulate these portions of the ablation balloon and prevent the transfer of energy from the pulmonary vein (e.g., an ostium 515 of the pulmonary vein 514) and a blood pool therein. Such embodiments increase the efficiency of the cryofluid as its specific heat capacity is used to absorb energy from the antrum 516 and not energy from non-target tissue areas, and the blood pool. Accordingly, less cryofluid (e.g., nitrous oxide) and ablation therapy time are required to achieve the same area and depth of ablation—also referred to as a zone of ablation 550. Moreover, in applications using other ablation methodologies such as radio frequency or direct current electroporation pulses, the non-conductive portions 537 may radiate the generated energy back into the ablation balloon 536 in such a way as to achieve focusing and/or amplification of the energy through conductive portion 538. In reference to irreversible electroporation ablation using direct current energy, the pulses of energy may be delivered to targeted tissue in various forms, such as one or more monophasic pulses, one or more bi-phasic pulses, etc.

In its expanded state shown in FIG. 5, ablation balloon 536 engages inner walls of target pulmonary vein 514. Through one or more ablation processes mentioned above, the ablation balloon produces a circumferential zone of ablation 550 along the inner wall of the pulmonary vein at an antrum 516. The ablation zone electrically isolates the target pulmonary vein 514 from left atrium 512L. To the extent that arrhythmiatic foci were located within the ablation zone, the arrhythmiatic foci are destroyed. To the extent the arrhythmiatic foci are located in the target pulmonary vein on the opposite side of the ablation zone from the left atrium, the electrical impulses produced by those foci are blocked or inhibited by the ablation zone.

In a typical ablation therapy, pulmonary veins are treated in accordance to their likelihood of having an arrhythmiatic foci. Often, all pulmonary veins are treated. The processes as described herein for a right superior pulmonary vein may be similarly reproduced for each of the three other pulmonary veins.

Once ablation therapy is complete, ablation balloon 536 may be contracted, and ablation balloon catheter 534 may be retracted back into introducer sheath 330 (see, e.g., FIG. 3). An electrophysiology catheter, or electrodes proximal and distal to the ablation balloon, may be used to verify the efficacy of the therapy prior to removal of the ablation balloon catheter 531. In various embodiments of the present disclosure, additional electrodes may also be positioned on a surface of the ablation balloon 536, either alone, or in conjunction with electrodes 238 and 240 (as shown in FIG. 2). Moreover, these various electrodes may be used before, during, and after the ablation therapy. For example, prior to the ablation therapy, the electrodes may be used to determine optimal positioning of the balloon to increase electrical isolation of the target pulmonary vein 514 from the left atrium 512L. During the ablation therapy, the electrodes may be used to track the ablation rate over the length of the ablation therapy. Specifically, the sensed data from the electrodes may be used to determine when sufficient isolation between the pulmonary vein and the left atrium has been accomplished, and subsequently ending the ablation therapy. Similarly, after completion of an ablation therapy, the electrodes may be used to determine the efficacy of the ablation therapy, and whether additional therapy applications may be required.

Ablation balloons have been developed for a variety of different applications and take a number of different forms. Aspects of the present disclosure may utilize ablation balloons of various types and mechanical construction. The ablation balloons can be either self-erecting or mechanically erected, such as through the use of an internal balloon. In one example embodiment, a lumen extending through a length of a shaft of the ablation balloon catheter 534 may inject a fluid into the ablation balloon which exerts a radial force on the ablation balloon—thereby expanding the balloon into an erect configuration (as shown in FIG. 5). Moreover, the conductive and nonconductive portions (538 and 537, respectively) of the balloon 536 may be located in various patterns, arrangements, and configurations across a surface of the ablation balloon as necessary for a given application. Some embodiments may not require conductive portions where a material of the balloon allows for transmission of the ablation energy, likewise, embodiments may not require non-conductive portions where the balloon material insulates the transmission of energy through the balloon. It is further understood that aspects of the present disclosure are directed to various implementations where the conductive and nonconductive portions (538 and 537, respectively) are integral to the expandable ablation balloon 536, coupled to inner and/or outer surfaces of the ablation balloon 536, and/or positioned within an interstitial space between the expanded ablation balloon 536 and shaft 534.

Figure 6:
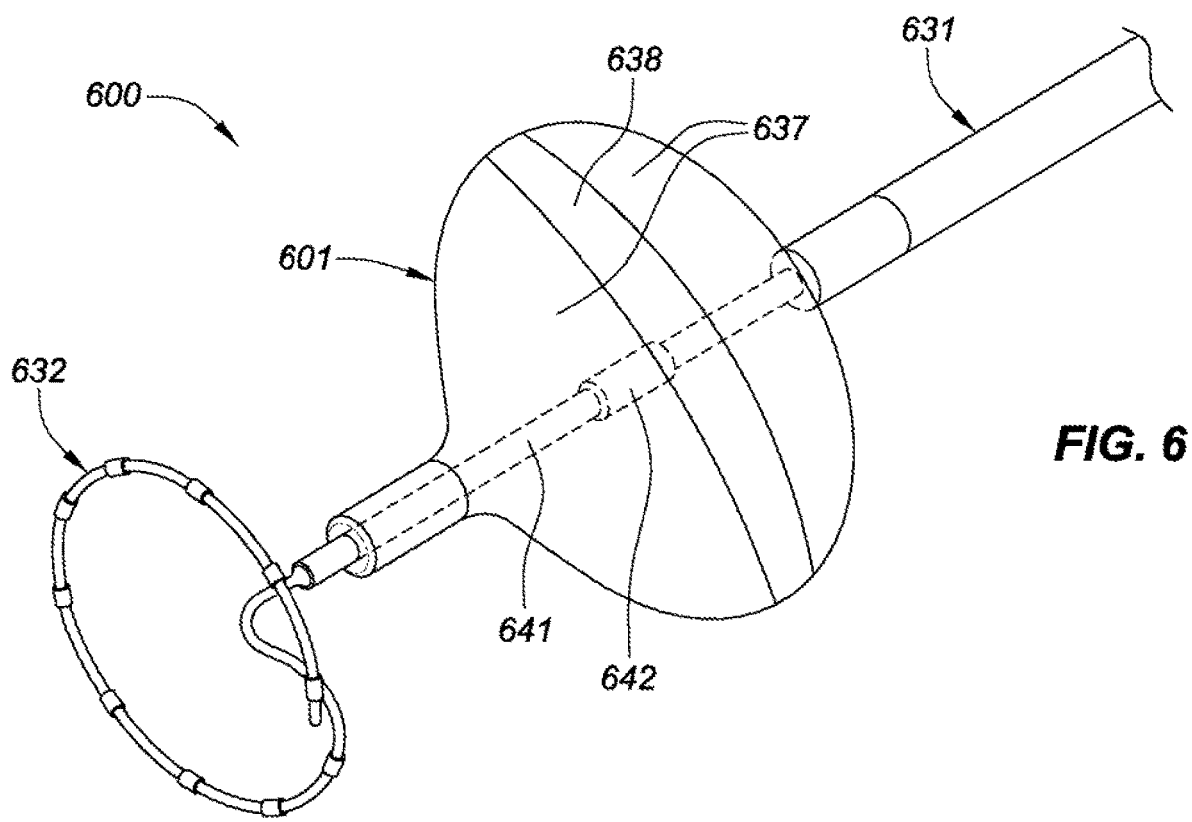
FIG. 6 is an isometric side view of a deployed ablation balloon catheter and an electrophysiology loop catheter extending through a central lumen of the ablation balloon catheter, consistent with various aspects of the present disclosure.

FIG. 6 is an isometric side view of an electrophysiological system 600 including a deployed ablation balloon catheter 631 and an electrophysiology loop catheter 632 extending through a central lumen 641 of the ablation balloon catheter, consistent with various aspects of the present disclosure. The deployed ablation balloon catheter 631 of the present embodiment includes a cryoablation balloon 601 with a fluid lumen that transports cryofluid the length of the shaft to a manifold 642 that circumferentially distributes cryofluid within the cavity of the ablation balloon 601. In various embodiments consistent with the present disclosure, the manifold 642 (or apertures therein) may be positioned to distribute the cryofluid in such a way as to focus the cryofluid at specific regions of the ablation balloon 601—for example, a distal, proximal, or intermediate portion of the balloon 601. In further more specific embodiments, the manifold 642 and/or apertures therein may be adjustable allowing a clinician to optimize a therapy given various conditions and a location of the ablation balloon 601 relative to a pulmonary vein.

Aspects of electrophysiological system 600 may be directed toward ablation therapies for pulmonary vein ostium, where a conductive portion 638 of the ablation balloon 601 contacts ostial tissue of the pulmonary vein and transfers heat from the tissue into the ablation balloon 601 in response to the ablation balloon being filled with cryofluid. The cryofluid, in response to a rapid pressure change as it enters the ablation balloon, undergoes a phase change from liquid to gas that requires a large amount of energy— thereby drawing energy from the pulmonary vein ostium in thermal communication thereto which ablates the ostial tissue.

To assist in focusing energy absorption by ablation balloon 601, adjacent either side of conductive portion 638, nonconductive portions 637 of the ablation balloon 601 insulate the tissue and blood pool in proximity thereto to prevent heat transfer which may cause unintentional/over ablation of pulmonary vein tissue. Nonconductive regions 637 also focus the energy absorption of the cryofluid phase change toward the desired tissue for ablation to help mitigate heat transfer variations that may affect the overall efficacy of the ablation therapy, as well as decrease cryofluid use for a given ablation therapy.

In various embodiments of the present disclosure, loop catheter 632 may be extended through a central lumen 641 of ablation balloon catheter 631 to measure the electrophysiological characteristics of a target pulmonary vein. Once the loop catheter 632 extends out of the central lumen 641, it can expand into a loop, with contact electrodes along the loop catheter contacting an inner surface of the pulmonary vein.

Figure 7:
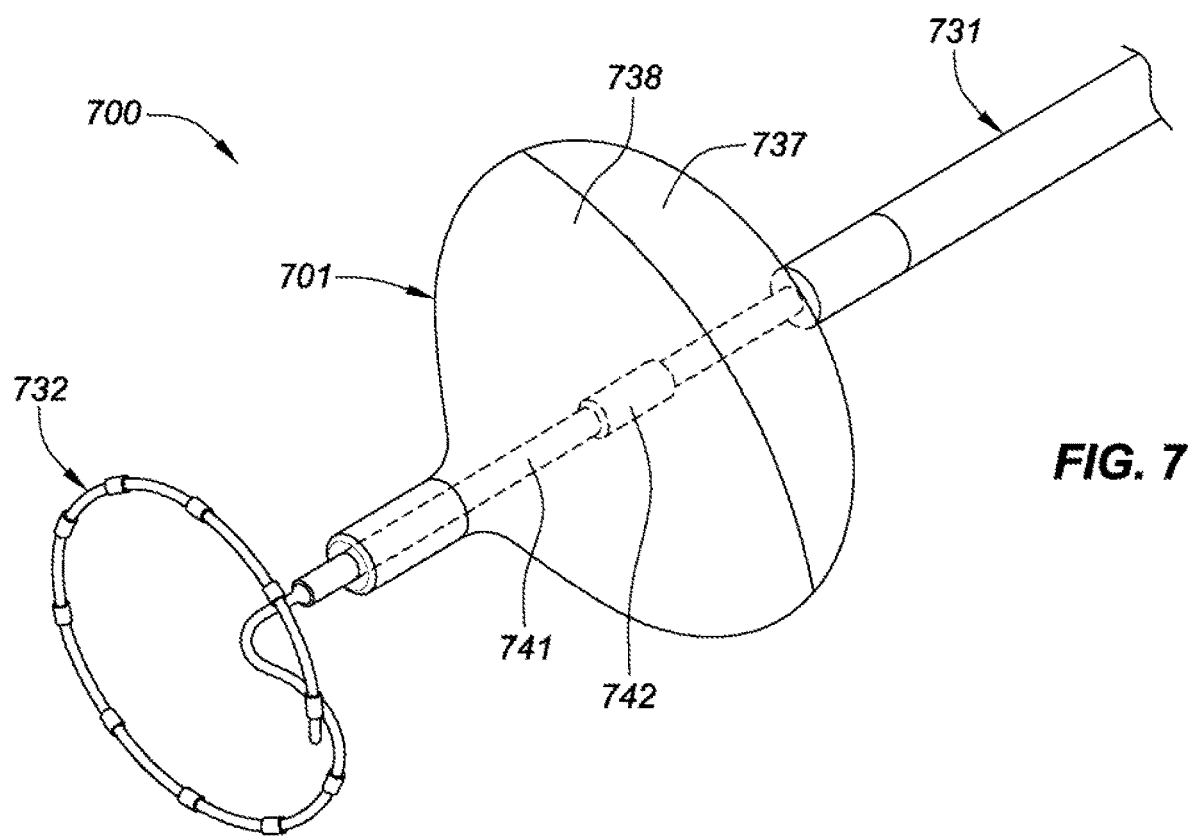
FIG. 7 is an isometric side view of a deployed ablation balloon catheter and an electrophysiology loop catheter extending through a central lumen of the ablation balloon catheter, consistent with various aspects of the present disclosure.

FIG. 7 is an isometric side view of an ablation balloon catheter 731 including a deployed ablation balloon 701 and an electrophysiology loop catheter 732 extending through a central lumen 741 of the ablation balloon catheter, consistent with various aspects of the present disclosure. The deployed ablation balloon 701 of the present embodiment is a cryoablation balloon with a fluid lumen that transports cryofluid the length of the shaft to a manifold 742 that circumferentially distributes cryofluid within the cavity of the ablation balloon 701. In various embodiments consistent with the present disclosure, the manifold 742 may be positioned in such a way as to focus the cryofluid at specific regions of the ablation balloon 701—for example, in the present embodiment, the manifold 742 may direct the cryofluid toward a distal end of the ablation balloon 701.

Aspects of electrophysiological system 700 may be directed toward ablation therapies for a pulmonary vein atrum—a conductive portion 738 of ablation balloon 701 may be placed into contact with the pulmonary vein antrum and transfer heat from the tissue into the ablation balloon 701 in response to the ablation balloon being filled with cryofluid. To assist in focusing the energy absorption by ablation balloon 701, nonconductive portion 737 at a proximal end of the ablation balloon insulates the blood pool in contact with the distal portion of the ablation balloon 701. Accordingly, the nonconductive region 737 focuses the ablative energy of the cryofluid toward the target pulmonary vein tissue in contact with the conductive portion 738. In more specific embodiments, the non-conductive portion 737 may also include a parabolic reflective surface on an interior of the ablation balloon 701 which enhances the energy transfer from the pulmonary vein antrum to the ablation balloon 701. As discussed in reference to FIG. 6, loop catheter 732 may be extended through a central lumen 741 of ablation balloon catheter 731 to measure the electrophysiological characteristics near an antrum of a target pulmonary vein.

In various alternative embodiments consistent with FIGS. 5-7, ablation balloons 501, 601, and 701 may be deployed by filing a cavity within the balloon with a conductive fluid (e.g., saline). In such an embodiment, n electrode 642, 742 within the ablation balloon may be powered to transmit radio frequency waves, one or more direct current electric pulses, among other forms of energy through the conductive fluid and conductive regions 538, 638, and 738 of the ablation balloon to ablate tissue in contact with the conductive regions. As discussed above, non-conductive regions 537, 637, and 737 block or minimize the transfer of such energy to non-target tissue in contact therewith.

Figure 8:
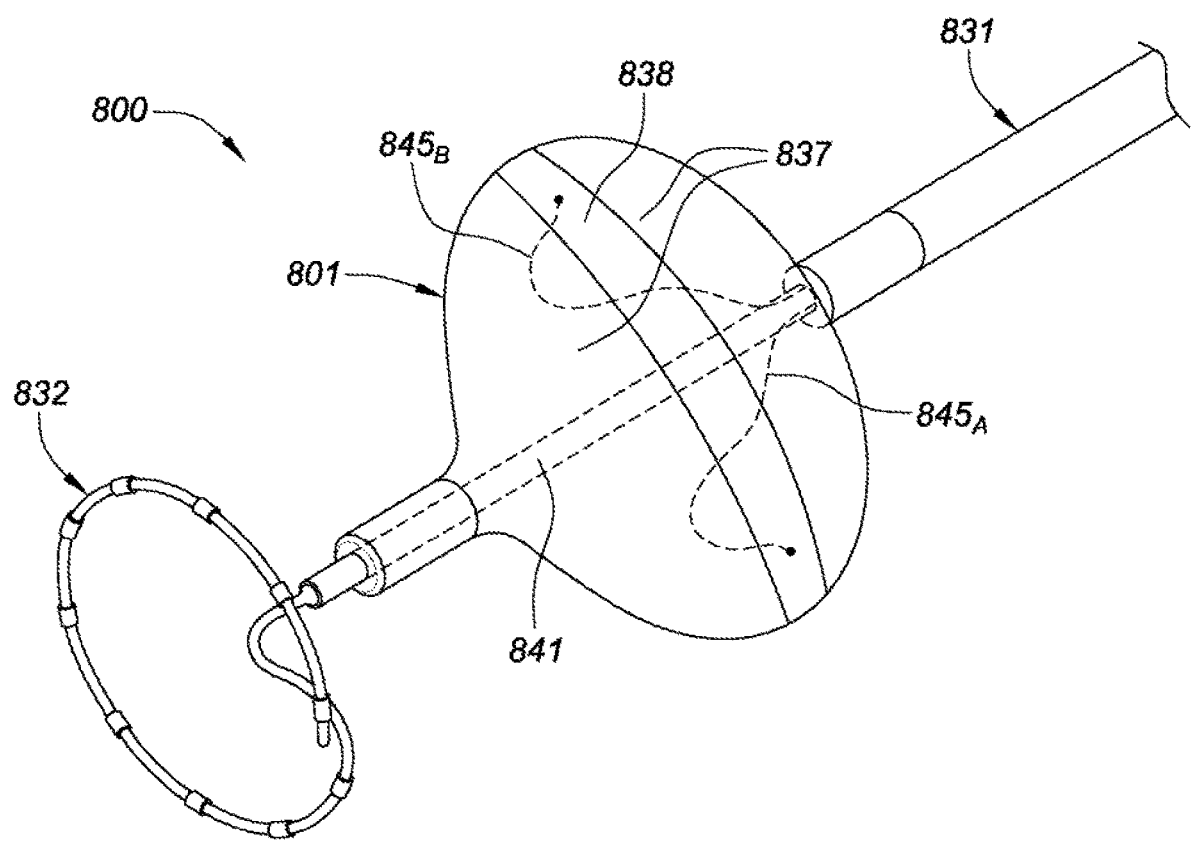
FIG. 8 is an isometric side view of a deployed ablation balloon catheter and an electrophysiology loop catheter extending through a central lumen of the ablation balloon catheter, consistent with various aspects of the present disclosure.

FIG. 8 is an isometric side view of an electrophysiological system 800 including a deployed ablation balloon catheter 831 and an electrophysiology loop catheter 832 extending through a central lumen 841 of the ablation balloon catheter 831, consistent with various aspects of the present disclosure. Aspects of the present disclosure are directed to an electroporation ablation balloon 801 which utilizes direct current applied across target pulmonary vein tissue to ablate tissue. Moreover, aspects of the present disclosure may be further directed to ablation therapies directed to a pulmonary vein ostium. In such embodiments, distal and proximal portions of ablation balloon 801 comprise non-conductive portions 837 that are electrically insulative. Between the non-conductive portions 837, a conductive portion 838 extends around a central circumferential section of the ablation balloon 801. The conductive portion 838 has a low electrical resistance that facilitates the flow of electrical current from the ablation balloon to tissue in contact therewith. In the present embodiment, the direct current is generated (by a signal generator) at a distal end of the catheter (outside the patient's body) and travels along two electrical leads $845_{A-B}$ through the catheter shaft and the ablation balloon 801, and into contact with the conductive portion 838. In some embodiments of the present disclosure, the ablation balloon 801 may include solder pads that facilitate the electrical leads $845_{A-B}$ being electrically coupled to the ablation balloon 801 using a solder. Various other electrical coupling methods are also readily apparent, including, for example, flexible circuitry and electrical connectors.

In some specific embodiments consistent with the disclosure of FIG. 8, ablation balloon 801 may consist of traditional catheter balloon polymers, with conductive portion 838 being attached to an external surface of the ablation balloon 801, and including wavy-structured electrodes coupled to the exterior surface and capable of expanding and contracting in conjunction with the ablation balloon. The electrodes being electrically coupled to the electrical leads $845_{A-B}$ by an electrical via that extends through the polymer balloon. In some specific embodiments, the ablation balloon 801 may be a stretchable electrical circuit with the electrodes printed on and extending across a surface thereof.

In yet further embodiments consistent with FIG. 8, a fluid used to inflate ablation balloon 801 may be a conductive fluid such as a saline solution. An electroporation pulse generated (by a signal generator, for example) at a proximal end of the catheter shaft may be transmitted up through a fluid-column within an electrically insulative fluid lumen of the shaft, through the ablation balloon 801, and into contact with conductive portion 838. In some embodiments, the electroporation pulse may be a direct-current pulse.

In various electroporation-based ablation balloon catheter embodiments, as disclosed herein, ablation balloon 801 may include one or more layers with pores located there between. For example, an inner layer of the balloon may be electrically insulative to prevent a flow of current from a volume of saline fluid used to expand the balloon 801. An outer layer of the balloon may be electrically conductive. The balloon may include one or more pore regions which extend circumferentially about a longitudinal axis of the balloon. Accordingly, where a clinician desires to ablate tissue in contact with a distal portion of the ablation balloon 801, a saline solution may be pumped into distal pores creating a conductive path to the target tissue. An electroporation pulse may be generated, and transmitted up through a fluid-column fluidly coupled to the saline filled distal pores, and into contact with the target tissue (via the conductive outer layer of the ablation balloon). To conduct subsequent ablation therapies at other tissue sites, the saline within the distal pores may be evacuated and another pore region (e.g., intermediary pore region) in contact with subsequent tissue for ablation may be filled with saline solution and an electroporation pulse delivered thereto.

In various embodiments of the present disclosure, an ablation balloon can be integrated onto a shaft of an electrophysiology hoop catheter (also referred to as a loop catheter). In yet other embodiments, an ablation balloon catheter may include a central lumen that allows for an electrophysiology hoop catheter to extend through the length of the ablation balloon catheter.

Embodiments consistent with the present disclosure may include ablation balloons that utilize radio frequency ablation techniques. In such embodiments, a radio frequency emitter may be located within the ablation balloon, such as in contact with a catheter shaft. The emitter transmitting radio frequency waves through a fluid within the ablation balloon, and a conductive portion of the ablation balloon, into contact with tissue adjacent the conductive portion. In some embodiments, the conductive portion is merely a polymer that allows for the transmission of radio waves. In various embodiments, where selective radiation of tissue with the radio waves is desirable, a portion of the ablation balloon surface may be, or include radio wave shielding materials that prevent the transmission of radio waves through the non-conductive portions—thereby facilitating selective radiation and ablation of tissue.

In some embodiments of the present disclosure, conductive portions of an ablation balloon may include electrodes (e.g., wavy electrodes) along a surface of the conductive portion of the ablation balloon to facilitate electrical transmission of the ablative energy to the tissue.

Various ablation balloon embodiments utilizing electroporation, and consistent with the present disclosure, may require 200 joules of energy with a max power of 5 kilowatts. In embodiments where the electroporation pulses travel up a fluid column in a catheter shaft, the requirements may be higher based on the electrically insulative characteristics of the fluid lumen.

In various embodiments of the present disclosure, a conductive portion of an ablation balloon may include a polymer with embedded nickel or other metallic dust. The conductive portion may also be a conductive polymer that is formed using at least some conductive materials and which is conductive even in its quiescent state, such that the polymer may conduct sufficient energy to ablate tissue. Aspects of the present disclosure are amenable to various conductive polymer materials. For example, U.S. Pat. No. 6,999,821, which is hereby incorporated by reference as though fully set forth herein, discloses intrinsically conductive and conductor-filled polymers that may be useful in the present invention. As disclosed therein, intrinsically conductive polymers include polyacetylene, polypyrrole, and polyanaline, among others. Conductor-filled polymers may include presently available materials approved for implantation such as silicone rubber with embedded metallic, carbon or graphite particles or powder. Silver filled silicone rubbers of the kind manufactured by NuSil or Specialty Silicone Products, modified so as to be approved for implantation, are of potential utility. An example is silver-coated, nickel-filled silicone rubber sold as NuSil R2637.

The substrate of a conductive portion of an ablation balloon need not be silicone; for example, it is contemplated that other insulating or weakly conductive materials (e.g., non-conductive elastomers) may be embedded with conductive materials, conductive alloys, and/or reduced metal oxides (e.g., using one or more of gold, silver, platinum, iridium, titanium, tantalum, zirconium, vanadium, niobium, hafnium, aluminum, silicone, tin, chromium, molybdenum, tungsten, lead, manganese, beryllium, iron, cobalt, nickel, palladium, osmium, rhenium, technetium, rhodium, ruthenium, cadmium, copper, zinc, germanium, arsenic, antimony, bismuth, boron, scandium, and metals of the lanthanide and actinide series, and, if appropriate, at least one electroconductive agent). The conductive material may be in the form of powder, grains, fibers, or other shaped forms. The oxides can be mixtures comprising sintered powders of an oxycompound. The alloy may be conventional; for example, titanium boride.

Other examples of conductive polymers that may be used in the present invention include the conductive polymers described and disclosed in U.S. Pat. Nos. 6,646,540, 6,495,069, and 6,291,568, all of which are incorporated by reference as if set forth in their entireties herein.

The conductive polymer may be pressure sensitive, in that the electrical resistance of the electrode may vary inversely in proportion to the pressure that is applied thereto. It should be understood, however, that the flexible conductive polymer electrodes disclosed herein are conductive even in their quiescent state (that is, when not under stress), and are therefore distinguished from the pressure sensitive conductive composite ("PSCC") electrodes disclosed in, for example, U.S. Pat. No. 7,955,326, which are non-conductive in their quiescent state. Preferably, the conductive polymer material will also meet cytotoxity, hemolysis, systemic toxicity and intracutaneous injection standards.

Other examples of conductive polymers that may be used in the present invention include the conductive polymers described and disclosed in U.S. Pat. No. 8,500,731, which is hereby incorporated by reference as though fully set forth herein. The insulative sheath of the catheter shaft may be preferably made of a biocompatible electrically insulative material, including, for example, a polymeric material, such as an extruded polytetrafluoroethylene (PTFE) tubing (e.g., Teflon® brand tubing).

Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation balloon apparatus, the apparatus comprising:
 a catheter shaft including proximal and distal ends;

an ablation balloon including proximal and distal ends, the proximal end of the ablation balloon coupled to the distal end of the catheter shaft, the ablation balloon including:
   a balloon surface;
   an ablation portion comprising a conductive baffle configured to facilitate energy transfer between the ablation balloon and tissue in contact with the ablation portion to deliver ablation therapy along a circumference of a pulmonary vein, wherein the conductive baffle is repositionable, via a pull wire, between i) a first position at a central portion of the ablation balloon and ii) a second position at a distal portion of the ablation balloon, and
   a non-ablation portion configured to mitigate energy transfer between the ablation balloon and tissue in contact with the non-ablation portion; and
   a plurality of electrical leads extending from the proximal end of the catheter shaft through the length of the catheter shaft, the plurality of electrical leads electrically coupled to the ablation portion; and
a signal generator electrically coupled to the proximal end of the plurality of electrical leads, wherein the signal generator is configured to transmit an electroporation pulse through the electrical leads to the ablation portion of the ablation balloon and ablate tissue in contact with the ablation portion.

2. The apparatus of claim 1, wherein the ablation portion of the ablation balloon is configured to
   engage a circumferential portion of a pulmonary vein, and ablate tissue along the circumferential portion of the pulmonary vein in contact with the ablation portion.

3. The apparatus of claim 1, further including a second non-ablation portion situated at a proximal end of the ablation balloon, and wherein the ablation portion of the ablation balloon is situated between the non-ablation portion and the second non-ablation portion, and the ablation portion is configured to deliver a tissue ablation therapy along a circumference of a pulmonary vein ostium.

4. The apparatus of claim 1, wherein the ablation portion is situated at a distal end of the ablation balloon, and the non-ablation portion is situated adjacent to the ablation portion at a proximal end of the ablation balloon, and the ablation portion is configured to deliver a tissue ablation therapy along a circumference of a pulmonary vein antrum.

5. The apparatus of claim 1, wherein the ablation balloon consists of a polymer material, and the ablation portion of the ablation balloon includes metallic dust within the polymer material.

6. The apparatus of claim 1, further including a central lumen extending through the length of the catheter shaft from the distal to the proximal end, the central lumen configured to receive a diagnostic catheter.

7. A balloon catheter for pulmonary vein isolation comprising:
   a steerable balloon delivery catheter shaft configured to deploy an ablation balloon into a pulmonary vein;
   wherein the ablation balloon is coupled to a distal end of the balloon delivery catheter shaft, the ablation balloon includes a balloon surface and an ablation portion comprising a conductive baffle configured to deliver irreversible electroporation ablation therapy, wherein the conductive baffle is repositionable, via a pull wire, between i) a first position at a central portion of the ablation balloon and ii) a second position at a distal portion of the ablation balloon, and the ablation balloon is configured to:
   deploy from an undeployed configuration, and
   engage a tissue wall of the pulmonary vein along the ablation portion of the ablation balloon.

8. The balloon catheter of claim 7, wherein the ablation portion is at a distal end of the ablation balloon, and the ablation balloon further includes a non-conductive portion proximal the distal ablation portion, the ablation portion configured to engage an antral circumference of the pulmonary vein and to conduct tissue ablation therapy of the pulmonary vein in contact with the ablation portion, the non-ablation portion configured to insulate a blood pool and pulmonary vein tissue in contact with the non-ablation portion from the ablation therapy.

9. An ablation balloon apparatus comprising:
   a catheter shaft including proximal and distal ends; and
   an ablation balloon including proximal and distal ends, the proximal end of the ablation balloon coupled to the distal end of the catheter shaft, the ablation balloon including
   a balloon surface; and
   an ablation portion comprising a conductive baffle configured to facilitate the transfer of one or more irreversible electroporation pulses between the ablation balloon and tissue in contact with the ablation balloon, wherein the conductive baffle is repositionable, via a pull wire, between i) a first position at a central portion of the ablation balloon and ii) a second position at a distal portion of the ablation balloon.

10. The ablation balloon apparatus of claim 9, wherein the ablation portion extends circumferentially about the ablation balloon.

11. The ablation balloon apparatus of claim 9, wherein the ablation portion is further configured to
   engage a circumferential portion of a pulmonary vein, and ablate tissue along the circumferential portion of the pulmonary vein in contact with the ablation portion.

12. The ablation balloon apparatus of claim 9, further including a signal generator configured to transmit one or more direct current pulses to the ablation portion of the ablation balloon.

13. The ablation balloon apparatus of claim 9, further including
   a plurality of electrical leads extending from the proximal end of the catheter shaft, through the length of the catheter shaft, and electrically coupled to the ablation portion; and
   a signal generator electrically coupled to the proximal end of the plurality of electrical leads, and configured to
   transmit one or more of the electroporation pulses through the electrical leads to the ablation portion of the ablation balloon, and
   ablate tissue in contact with the ablation portion.

14. The ablation balloon apparatus of claim 13, wherein the one or more electroporation pulses include a biphasic pulse.

15. The ablation balloon apparatus of claim 13, wherein the one or more electroporation pulses include a monophasic pulse.

16. The ablation balloon apparatus of claim 13, wherein the one or more electroporation pulses delivers 200 joules of energy with a max power of 5 kilowatts to the tissue.

\* \* \* \* \*